(12) United States Patent
Patno et al.

(10) Patent No.: US 7,888,107 B2
(45) Date of Patent: Feb. 15, 2011

(54) SYSTEM USING SELF-CONTAINED PROCESSING MODULE FOR DETECTING NUCLEIC ACIDS

(75) Inventors: Tim Patno, Chicago, IL (US); Tom Westberg, Gurnee, IL (US); Mark Weber, Algonquin, IL (US); Benjamin Rush, Evanston, IL (US); Christopher Khoury, Columbus, OH (US); David Morrow, Chicago, IL (US); Janusz Ruszel, Waukegan, IL (US); Christian Kronshage, Round Lake, IL (US); William Cork, Lake Bluff, IL (US)

(73) Assignee: Nanosphere, Inc., Northbrook, IL (US)

( * ) Notice: Subject to any disclaimer, the term of this patent is extended or adjusted under 35 U.S.C. 154(b) by 1240 days.

(21) Appl. No.: 11/491,564

(22) Filed: Jul. 24, 2006

(65) Prior Publication Data

US 2011/0008907 A1    Jan. 13, 2011

(51) Int. Cl.
*C12M 3/00* (2006.01)
*C12M 1/34* (2006.01)

(52) U.S. Cl. .............. 435/287.2; 435/287.8; 435/287.9; 435/288.1; 435/288.3; 435/288.4; 435/288.5

(58) Field of Classification Search ............... 435/287.2
See application file for complete search history.

(56) References Cited

U.S. PATENT DOCUMENTS

| 5,587,128 | A | 12/1996 | Wilding et al. |
| 2001/0053525 | A1 | 12/2001 | Chu |
| 2002/0123059 | A1* | 9/2002 | Ho .............................. 435/6 |
| 2004/0086872 | A1* | 5/2004 | Childers et al. ............... 435/6 |

FOREIGN PATENT DOCUMENTS

| WO | WO 01/51207 | 7/2001 |
| WO | WO 01/83385 | 11/2001 |
| WO | WO 2004/015089 | 2/2004 |
| WO | WO 2004/020621 | 3/2004 |
| WO | WO 2004/020975 | 3/2004 |

\* cited by examiner

*Primary Examiner*—Walter D Griffin
*Assistant Examiner*—Lydia Edwards
(74) *Attorney, Agent, or Firm*—Gregory T. Pletta (57) ABSTRACT

A method and apparatus are provided for processing a nucleic acid. The apparatus includes a disposable self-contained processing module that contains the nucleic acid and substantially all of the fluids to effect a nanoparticle hybridization test, a pump coupled to the processing module, a valving system disposed between the pump and processing module and a control system coupled to the pump and valving system causing the processing fluids to interact with the nucleic acid to effect a sandwich hybridization test using nanoparticles.

33 Claims, 5 Drawing Sheets

SYSTEM USING SELF-CONTAINED PROCESSING MODULE FOR DETECTING NUCLEIC ACIDS

FIELD OF THE INVENTION

The field of the invention relates to biological testing and more particularly to detecting nucleic acids.

BACKGROUND OF THE INVENTION

Methods of detecting nucleic acids are generally known. In fact, there are a number of methods available for detecting specific nucleic acid sequences.

Known methods include those based upon electrophoresis, polymerase chain reaction (PCR) processes, various hybridization techniques, and a number of other techniques. While these methods are effective, they are all time consuming, costly and subject to significant human error.

For example, one manufacturer makes a microfluidics system that hybridizes a sample to a chip followed by staining of the chip. The hybridization process takes approximately 12 hours. Staining takes approximately 1.5 hours to complete.

Another supplier provides a system that relies upon a single nucleotide polymorphism (SNP) technique. This system uses a microchip for performing multiple assays. Probes are added to a cartridge and the particles move based on charge in an electric field. A detection system may be used for analyzing the cartridges after hybridization with the sample DNA.

Still another supplier provides a device called a Lightcycler that combines PCR amplification and DNA detection into one process. The Lightcycler can use one of two processes for detection. The first process relies upon PCR and hybridization. The second process relies upon PCR and dye and melting curve analysis.

The development of reliable methods for detecting and sequencing nucleic acids is critical to the diagnosis of genetic, bacterial and viral diseases. Because of the importance of health care and disease prevention, a need exists for quicker and cheaper methods of identifying nucleic acids.

SUMMARY

A method and apparatus are provided for processing a nucleic acid. The apparatus includes a disposable self-contained processing module that contains the nucleic acid and substantially all of the fluids to effect a nanoparticle hybridization test, a pump coupled to the processing module, a valving system disposed between the pump and processing module and a control system coupled to the pump and valving system causing the processing fluids to interact with the nucleic acid to effect a sandwich hybridization test using nanoparticles.

BRIEF DESCRIPTION OF THE DRAWINGS

FIG. 4(a)-4(l) is an overlay diagram of the processing module of FIG. 3; and

DETAILED DESCRIPTION OF AN ILLUSTRATED EMBODIMENT

Figure 1:
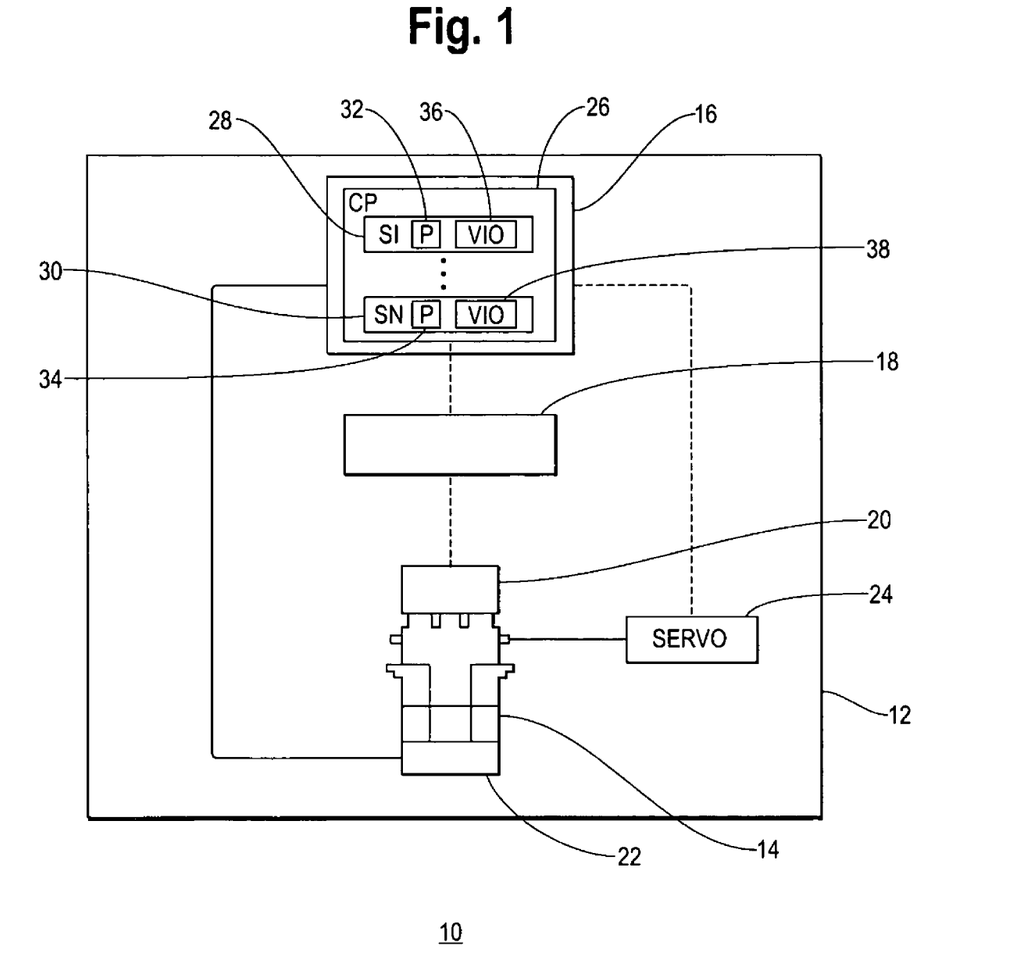
FIG. 1 is a block diagram of a system for detecting nucleic acids in accordance with an illustrated embodiment of the invention.

FIG. 1 is a perspective view of a nucleic acid detection system 10, shown generally in accordance with an illustrated embodiment of the invention. The processing system 10 may be used for the detection of any of a number of predetermined target nucleic acids using sandwich hybridization testing. In fact, any type of nucleic acid may be detected, and the methods may be used for the diagnosis of disease and in sequencing of nucleic acids. Examples of nucleic acids that can be detected by the methods of the invention include genes (e.g., a gene associated with a particular disease), viral RNA and DNA, bacterial DNA, fungal DNA, cDNA, mRNA, RNA and DNA fragments, oligonucleotides, synthetic oligonucleotides, modified oligonucleotides, single-stranded and double-stranded nucleic acids, natural and synthetic nucleic acids, etc. Examples of the uses of the methods of detecting nucleic acids include: the diagnosis and/or monitoring of viral diseases (e.g., human immunodeficiency virus, hepatitis viruses, herpes viruses, cytomegalovirus, and Epstein-Barr virus), bacterial diseases (e.g., tuberculosis, Lyme disease, *H. pylori, Escherichia coli* infections, *Legionella* infections *Mycoplasma* infections, Sammonella infections), sexually transmitted diseases (e.g., gonorrhea), inherited disorders (e.g., cystic fibrosis, Duchene muscular dystrophy, phenylketonuria, sickle cell anemia), and cancers (e.g., genes associated with the development of cancer); in forensics; in DNA sequencing; for paternity testing; for cell line authentication; for monitoring gene therapy; and for many other purposes.

The sample processing system 10 may include a number of functionally distinct elements used for processing samples. For example, the processing system 10 includes a processing controller 12 and a disposable, self-contained processing module 14. As used herein, a self-contained processing module means that the module contains the DNA or RNA sample as well as all of the processing liquids needed to carry the process for detecting nucleic acids to completion and which internally stores any waste liquids produced during the process.

The processing of the DNA or RNA sample occurs within a hybridization chamber (generally designated by reference number 204 in the attached drawings) located within the processing module 14. The processing liquids are initially located in one or more liquid wells disposed within a body of the processing module 14. Processing occurs by causing the processing liquids to sequentially flow among liquid wells and/or between the liquid wells and hybridization chamber as described in more detail below.

Once the process for detecting nucleic acids has been carried to completion, the processed sample may be read by an optical reader. The optical reader may be a model Verigene ID™ made by Nanosphere, Inc. of Northbrook, Ill.

In general, the processing controller 12 includes a central processing unit (CPU) 16, a servo actuator 24, a pump 18 and heating/cooling devices 22. The servo 24, pump 18 and heating/cooling devices 22 function under control of the CPU 16. The servo 24 creates fluid paths that route processing fluids through the processing module 14 while the pump 18 moves the processing liquids through the created paths.

The pump 18 may operate under any of a number of different formats. For example, the pump 18 may include a separate pumping unit for each fluid path. Alternatively, a single pump may be used and separate valves provided to route fluids through the fluid paths.

Under one illustrated embodiment, the pump 18 may be a positive displacement pump (e.g., a syringe pump) coupled to a valve manifold (FIG. 5) that include a number of solenoid-operated pneumatic valves V1-V12 that generates a separate pneumatic signal for each fluid path created by the servo 24. In order to prevent cross-contamination between the pump 18 and processing module 14, the pump 18 may use air pressure as a medium to pump the processing liquids through the created paths. Air pressure from the pneumatic valves V1-V12 is applied to the processing module 14 through a pneumatic coupler 20.

Figure 2:
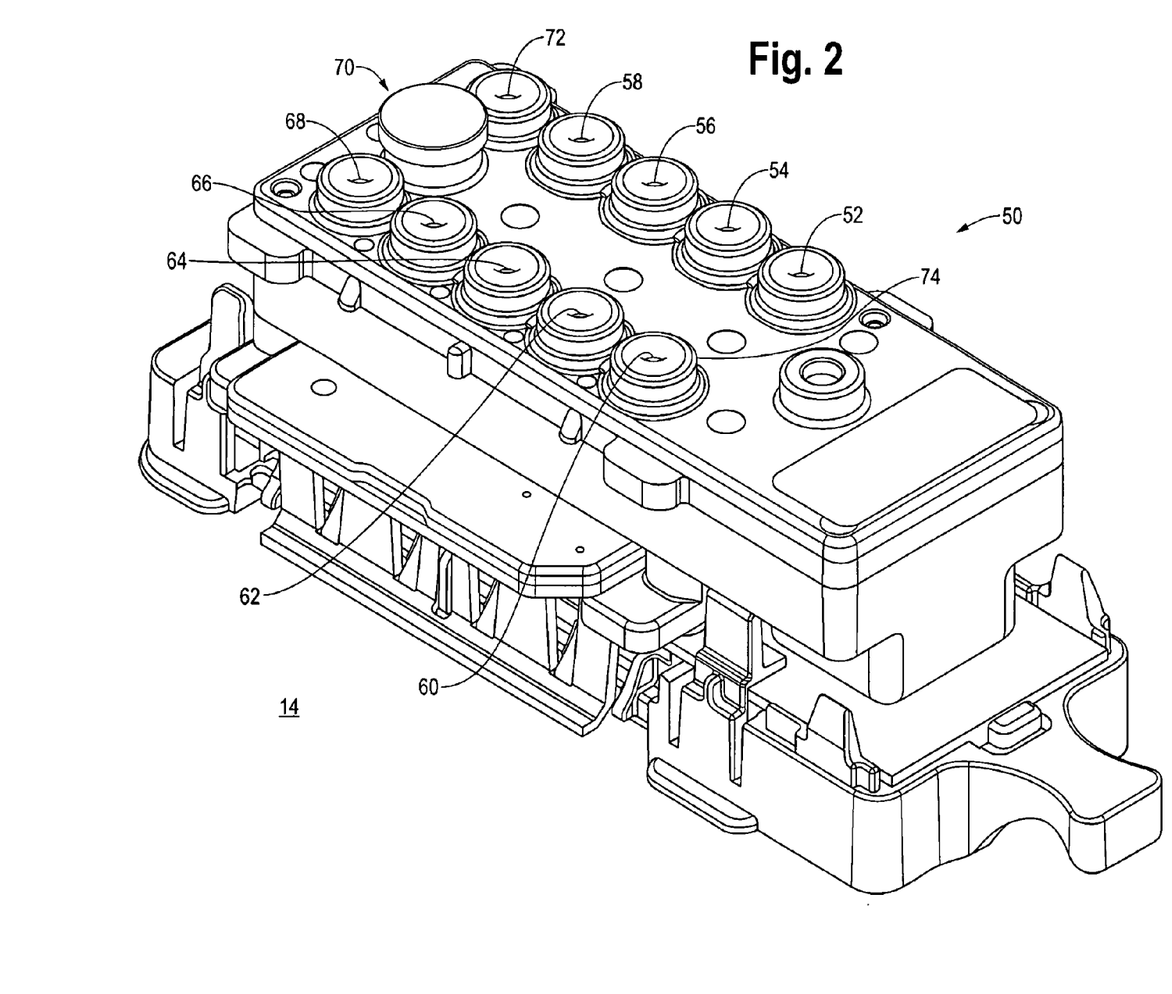
FIG. 2 is a top perspective view of a processing module that may be used with the system of FIG. 1.
Figure 3:
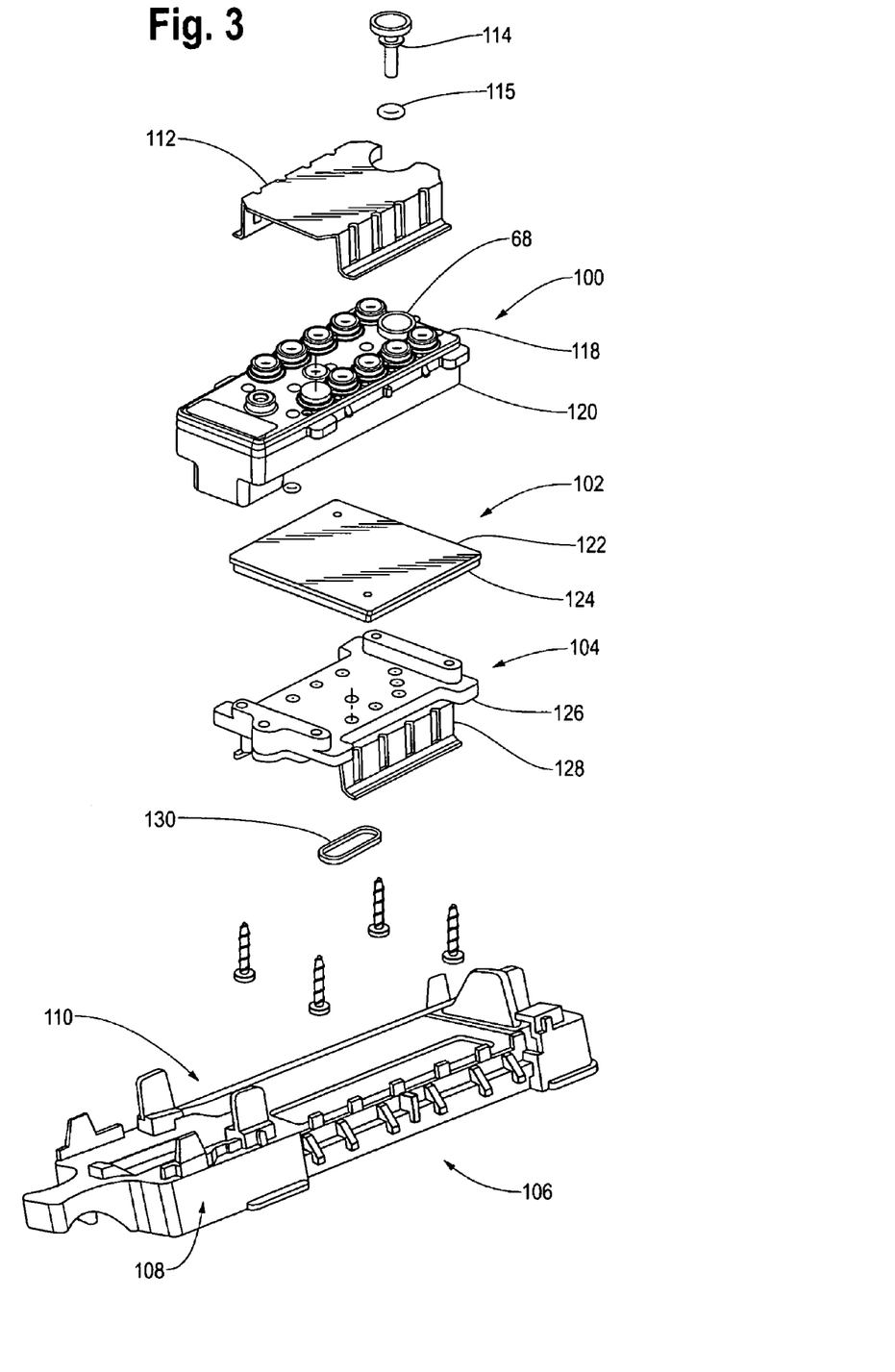
FIG. 3 is an exploded side perspective view of the processing module of FIG. 2.

FIG. 2 is a side perspective view of the processing module 14 and FIG. 3 is an exploded view of the processing module 14. As shown in FIG. 3, the processing module 14 includes a reagent container assembly 100, a valve plate 102, a manifold assembly 104 and a substrate assembly 106. The substrate assembly 106 includes a substrate 110 and a substrate holder 108.

It should be noted that a hybridization chamber 204 is formed between a lower surface of the manifold cover 128 and an upper surface of the substrate 110. A periphery of the hybridization chamber 204 is defined by the hybrization gasket 130.

Figure 4A:
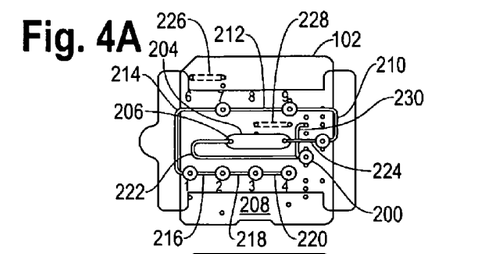
Figure 4B:
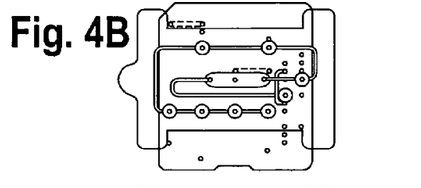
Figure 4C:
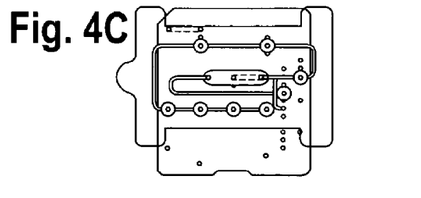
Figure 4D:
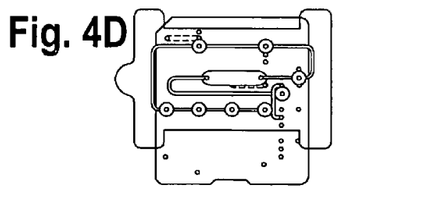
Figure 4E:
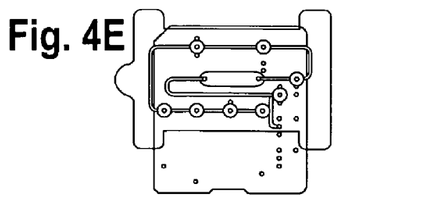
Figure 4F:
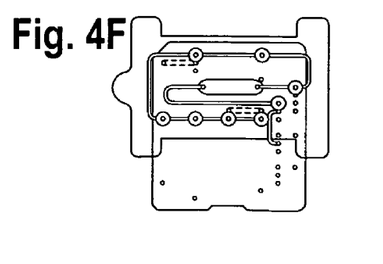
Figure 4G:
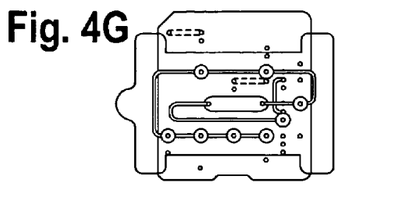
Figure 4H:
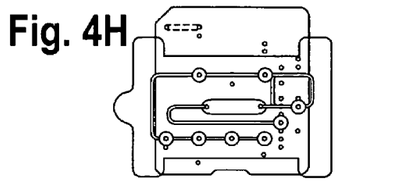
Figure 4I:
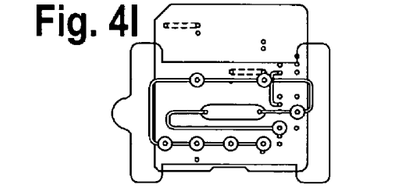
Figure 4J:
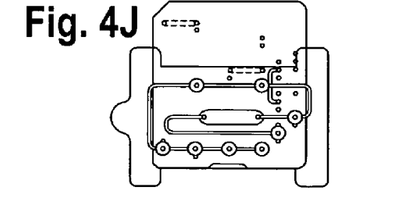
Figure 4K:
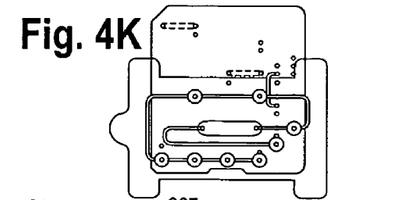
Figure 4L:
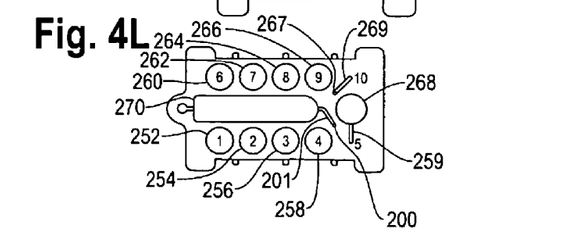

The reagent container assembly 100 includes a cover 118 and a container body 120 that includes a number of liquid wells 50 (FIG. 2). FIG. 4(*l*) shows a top view of the container body with the cover removed to reveal the liquid wells 252, 254, 256, 258, 260, 262, 264, 266, 268, 270.

The liquid wells 50 may each be of sufficient size to contain an adequate quantity of processing liquid (e.g., 200 microliters). Within the group of liquid wells 50, a first well 268 may be a sample well into which a DNA or RNA sample is placed. Similarly, a second well 252 may contain 200 microliters of a target wash (Wash B), a third well 254 may contain 200 microliters of a probe wash (Wash D), a fourth well 256 may contain 200 microliters of water, a fifth well 258 may contain 200 microliters of a probe wash (Wash B), a sixth well 260 may contain 100 microliters of a first silver solution (AgA), a seventh well 262 may contain 100 microliters of a second silver solution (AgB), an eighth well 264 may contain 200 microliters of a probe and a ninth well 266 may contain 100 microliters of a hybridization buffer (2× Hyb Buffer).

Figure 5:
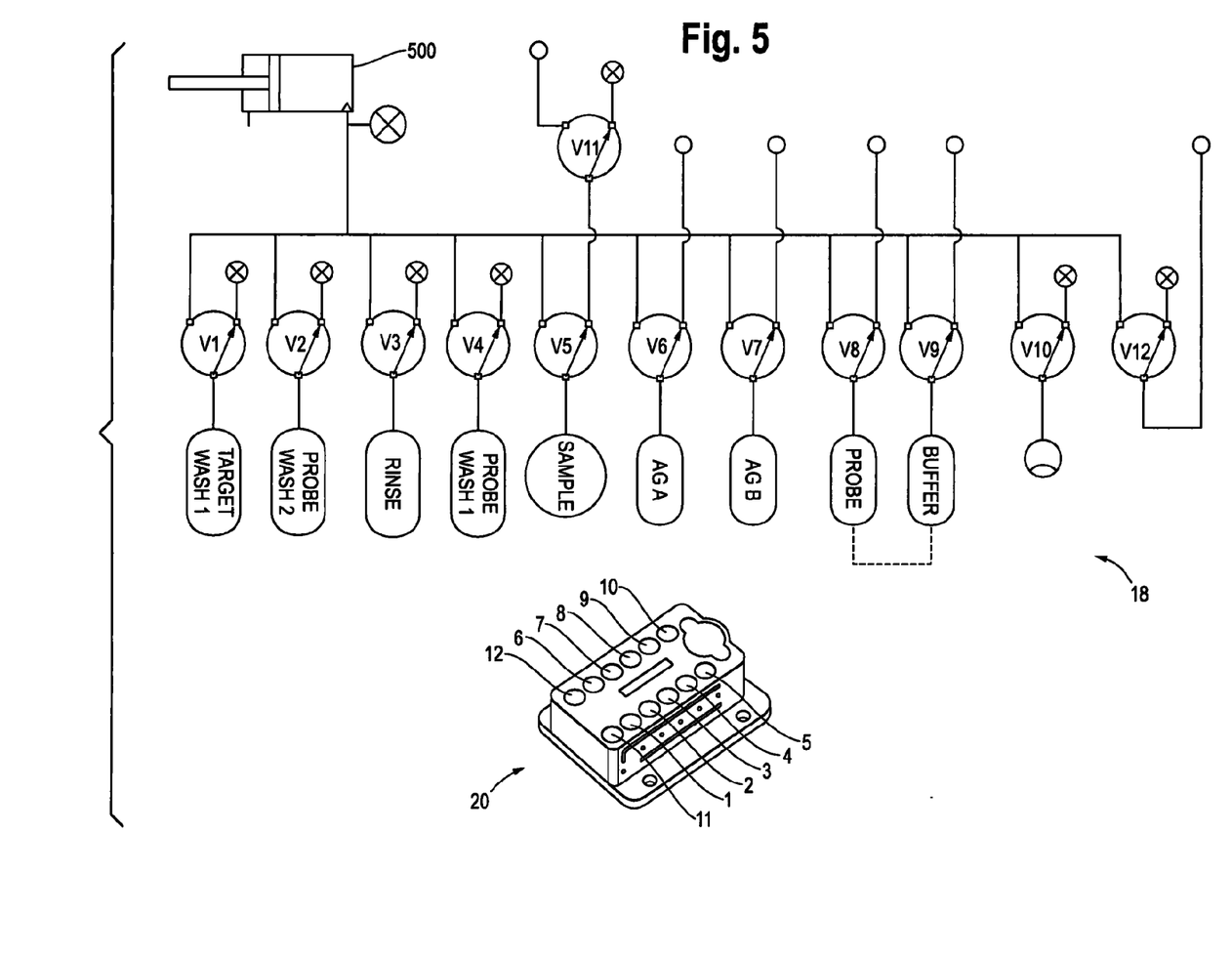
FIG. 5 is a schematic of a pneumatic distribution system used with the processing module of FIG. 2.

The numbers 1-9 (FIG. 4(*l*)) inside the wells 252, 254, 256, 258, 260, 262, 264, 266 are valve numbers that correspond to the valves shown in FIG. 5. For example, when activated by the CPU 16, valve V1 in FIG. 5 provides compressed air pressure from the pump of FIG. 5 to port #1 of the valve manifold 20, which in turn, introduces compressed air into pneumatic connection 52 in FIG. 2. Since pneumatic connection 52 is directly coupled to liquid well 252, the introduction of compressed air through connection 52 also pressurizes liquid well 252. Similarly, valve V2 connects to port #2 of manifold 20 and introduces compressed air into connection 54 and liquid well 254 on the module 14, valve V3 imparts air pressure to connection 56 and liquid well 256 and valve V4 provides pressure to connection 58 and liquid well 258. When deactivated, valves V1, V2, V3 and V4 are connected to blocked passageways.

Valve V6 provides pressure to connection 60 (and liquid well 260) when activated and is connected to atmosphere where deactivated. Similarly valve V7 provides pressure to connection 62 (and liquid well 262), valve V8 to connection 64 (liquid well 264) and valve V9 to connection 66 (liquid well 266) when activated and are each connected to atmosphere when deactivated.

Valve V5 provides pressure to the sample well 268 on the module 14 through connection 72 when activated. When valve V5 is deactivated, the sample well 268 can be independently vented to atmosphere through valves V5 and V11.

The sample module 14 may be filled with the liquids described above during a separate process in an environment where exposure to the DNA or RNA sample may be strictly controlled (treated as a biohazard). Once filled, the pneumatic connections 52, 54, 56, 58, 60, 62, 64, 66, 68, 72 may be sealed with a cartridge cover 112.

It should be noted in this regard that an O-ring 74 is provided within an upper lip of each of the pneumatic connections 52, 54, 56, 58, 60, 62, 64, 66, 68, 72 to form a seal with the cover 112. It should also be noted that the sample connection 70 has its own sample well cover 114 (FIG. 3) with its own O-ring or gasket 115 to form a seal with the sample connection 70 and to protect handlers from the content of the sample well 268.

Shown below the sample well 100 in FIG. 3 is the valve plate 102. In general, the valve plate 102 is activated (i.e., moved) by the servo 24 and functions to open and close a number of liquid conduits between the liquid wells 50 and/or between the sample wells 50 and the hybridization chamber 204.

FIGS. 4(*a-k*) are overlays of the operative elements of the processing module 14. The grey shaded areas in FIGS. 4(*a-k*) depict the relative position of the valve plate 102. FIG. 4(*a*) is a home position.

While FIG. 4 shows 11 positions of the valve plate 102, it should be understood that the processing module 14 and valve plate 102 may use any number of positions. Each position of the valve plate 102 creates a different flow conduit or flow conduits for processing the test sample. In general, the flow conduits are associated with respective liquid wells and are intended to cause a predetermined interaction of the content of one liquid well with a content of another liquid well or with a content of the hybridization chamber 204.

The interaction of liquids and the sequence of interactions is determined by the particular objective of the test procedure. While the liquid wells will be described in terms of use with a particular type of liquid, it should be understood that any liquid may be used in any one of the liquid wells.

In addition, while the sequence of use of the liquids and the conduits created for their use will be described in a particular order, it should be understood that the conduits may be created in any order based upon the test objective and the contents of the liquid wells. In this regard, the CPU 16 includes a computer program 26 that creates the conduits and pumps the liquids through the conduits in a manner determined by the program.

Within the program 26 is a number of program steps 28, 30. Associated with each program step 28, 30 is a position 32, 34 of the valve plate 102 and a valve identifier or valve identifiers 36, 38 associated with the program step. The positions 32, 34 identify a position of the valve plate 102 and are used by the servo 24 under control of the CPU 16 to move the valve plate into that position. The valve identifiers 36, 38 are used by the CPU 16 to activate the identified valves V1-V12.

Also included within each program step may be a pump instruction (not shown). The pump instruction may include a pumping rate and/or direction (in the case of a positive displacement pump).

FIGS. 4(*a*)-4(*k*) show exemplary positions of the valve plate 102, as defined by the program steps 28, 30. The first line of the description (shown immediately to the right of the overlays in FIGS. 4(*b-k*) shows a relative displacement of the valve plate 102 from the home position shown in FIG. 4(*a*).

The black dots on FIGS. 4(*a-k*) are holes (apertures) in the valve plate 102. The pairs of closely spaced, dotted lines on FIGS. 4(*a-k*) are channels 226, 228, 230 formed between a top plate 122 and a bottom plate 124 of the valve plate 102. As may be noted, the black dot on one end of channels 226, 230 (i.e., on the left end of channel 226 and the top of channel 230) is an aperture through only the top plate 122 in the valve plate 102 and the white-centered dot on the opposing end of the channels 226, 230 is an aperture through only the bottom plate 124 of the valve plate 102. The channel 228 is shown with black dots on opposing ends indicating that the channel 228 connects apertures through only the top plate 122.

The solid pairs of closely spaced, parallel lines in FIGS. 4(*a-k*) are channels 210, 212, 214, 216, 218, 220, 222, 224 formed in the manifold assembly 104 between the manifold base 126 and manifold cover 128. Channels 220, 218, 216, 214, 212 210, 224 form a continuous conduit within the manifold assembly 104 that is connected at a first end to the hybridization chamber 204 via aperture 208 in the manifold cover 128 and to the liquid wells 50 at various locations along its length via apertures in the upper surface of the manifold assembly 104 and corresponding apertures in the valve plate 102, the location of which depends upon the position of the valve plate 102.

The concentric circles on the overlays of FIGS. 4(*a-l*) represent the coincidence (vertical alignment) of apertures on the bottom of the liquid wells 50 and apertures on the top of the manifold base 126. In the case of the manifold base 126, the coincident apertures may be connected (depending upon the position of the valve plate 102) by corresponding apertures in the valve plate 102 that extend through the valve plate 102. Also shown in FIGS. 4(*a*) and 4(*l*), coincident apertures 200 are present on the bottom of the liquid well container 120 that extends through the container 120 to connect the waste well 270 to the manifold base 126 through the valve plate 102.

The coincident apertures 200 form a portion of a conduit between the hybridization chamber 204 and waste well 270. In this case the conduit is formed by channel 222 connected to the hybridization chamber 204 on a first end by aperture 206 and to the waste well 270 through the coincident apertures 200 and corresponding apertures in the valve plate 102.

Turning now to FIGS. 4(*a*)-4(*l*), FIG. 4(*a*) shows the valve plate 102 in the "home" position (zero displacement). In the home position, a user may load the module 14. The home position may also be used to heat and thereby denature the DNA or RNA sample or as a shipping and/or disposal position.

In the home position, a conduit is formed between the shuttle connection 68 (designated by valve reference 10 on the top surface of the module 14 (FIG. 4(*l*))) and the hybridization chamber 204. The conduit is formed by a shuttle connection 68, a lateral channel 269 between the container cover 118 and container 120, a vertical aperture 267 through the container 120, a corresponding aperture in the valve plate 102, channels 230 and 222 and aperture 206. Activation of the valve V10 and pump 500 causes pneumatic pressure to be applied to port 68 thereby moving fluids back through the hybridization chamber 204 via the formed conduit. The liquids within the hybridization chamber 204 may be shuttled back-and-forth through the hybridization chamber 204 by periodically reversing direction of the pump 500.

FIG. 4(*h*) shows the valve plate 102 in the +4.2 mm position. The +4.2 mm position may be used to mix a probe with a buffer. Movement of the valve plate 102 from the home position to the +4.2 mm position of FIG. 4(*h*) may be accomplished via operation of the servo 24 under control of the CPU 16.

In the +4.2 mm position, the channel 228 and apertures in the valve plate 102 on opposing ends of the channel 228 are located directly beneath (concentric with) the discharge apertures on the bottom of liquid wells 264, 266. As a consequence, the liquid well containing the probe (#8 in FIG. 4(*l*)) is connected to the liquid well containing the buffer (#9 in FIG. 4(*l*)) via the conduit formed by channel 228 and apertures on opposing ends of the channel 228. Activation of the valve V8 (and pump 500), therefore, causes the probe in liquid well 264 to be transported into and mixed with the buffer in the buffer liquid well 266.

It should be noted that in this example, that in a deactivated state, valve V9 is vented to atmosphere (FIG. 5), thereby venting the buffer well 266. To mix the probe and buffer, the controller 16 may alternately activate valves V8 and V9 to transfer the mixture between the liquid wells 264, 266.

FIG. 4(*c*) shows the valve plate 102 in the −4.2 mm position. As above, movement of the valve plate 102 from the +4.2 mm position to the −4.2 mm position of FIG. 4(*c*) may be accomplished via operation of the servo 24 under control of the CPU 16.

In the −4.2 mm position, the sample liquid well 268 is connected to the buffer sample well 266 via a conduit formed by the corresponding apertures in the bottom of the sample well 268 and buffer well 266, corresponding apertures in the valve plate 102 and channel 210. The sample may be moved to the buffer well 266 via the formed conduit.

In order to move the sample from the sample well 268 to the buffer well 266, pneumatic pressure may be applied by the sample well 268. Pneumatic pressure may be applied to the sample well 268 by the pump 500 through valve V5 pneumatic connection 72 and lateral channel 259.

The sample and buffer may be mixed by transferring the sample/buffer back to the sample well 268. Transfer back to the sample well may be accomplished by activating valves V9 and V11 and applying pneumatic pressure from the pump 500 through valve V9 and connection 66 to the buffer well 268. The sample/buffer may be further mixed by transferring the mixture back to the buffer well 266 as described above.

To move the sample/buffer mixture in the buffer well 266 to the hybridization chamber 204 or the sample/buffer/probe (from previous examples) to the hybridization chamber 204, the valve plate 102 may be moved to the −2.1 mm (FIG. 4(*b*)) position by the servo 24. In the −2.1 mm position, a conduit is formed between the buffer well 266 and hybridization chamber 204. In this case, the conduit includes concentric apertures in the buffer well 266, manifold assembly 104 and valve plate 102, channel 210 and aperture 208 on a first end of the hybridization chamber 204. Movement may be accomplished via pneumatic pressure applied to connection 66.

It should also be noted that in this example a venting conduit is also formed from the second, opposing end of the hybridization chamber 204. The venting conduit is formed through aperture 206 from the hybridization chamber 204 into channel 222 through coincident apertures 200 and corresponding aperture in the valve plate 102 and lateral channel 201 to the waste well 270.

Following transfer of the mixture from the buffer well 266 to the hybridization chamber 204, a target wash may be routed through the hybridization chamber 204. In order to route the target wash through the hybridization chamber 204, the valve plate 102 may be moved to the +6.3 mm position (FIG. 4(*i*)).

In the +6.3 mm position, a conduit is formed between the target wash well 252 and hybridization chamber 204 to the waste well 270. The conduit between the wash well 252 and hybridization chamber 204 includes the concentric apertures of the target wash well 252, valve plate 102 and manifold assembly 104, channels 214, 212, 210, 224 and aperture 208. The target wash is routed to the waste well 270 from the hybridization chamber 204 through a conduit formed from through aperture 206, channel 222, coincident apertures 200 and corresponding aperture in the valve plate 102 and lateral channel 201 to the waste well 270. The wash is urged through the hybridization chamber 204 into the waste well 270 via pneumatic pressure applied from the pump 500 through valve V1 and connection 52.

Following the target wash, a first probe wash may be routed through the hybridization chamber 204. In order to route the first probe wash through the hybridization chamber 204, the valve plate 102 may be moved to the +8.4 mm position (FIG. 4(*j*)).

In the +8.4 mm position, a conduit is formed between the probe wash well 258 and hybridization chamber 204 to the waste well 270. The conduit between the wash well 258 and hybridization chamber 204 includes the concentric apertures of the target wash well 258, valve plate 102 and manifold assembly 104, channels 220, 218, 216, 214, 212, 210, 224 and aperture 208. The probe wash is routed from the hybridization chamber 204 to the waste well 270 through a conduit formed from through aperture 206, channel 222, coincident apertures 200 and corresponding aperture in the valve plate 102 and lateral channel 201 to the waste well 270. The wash is urged through the hybridization chamber 204 into the waste well 270 via pneumatic pressure applied from the pump 500 through valve V4 and connection 58.

Following the first probe wash, a second probe wash may be routed through the hybridization chamber 204. In order to route the second probe wash through the hybridization chamber 204, the valve plate 102 may be moved to the +10.5 mm position (FIG. 4(*k*)).

In the +10.5 mm position, a conduit is formed between the probe wash well 254 and hybridization chamber 204 and also to the waste well 270. The conduit between the wash well 254 and hybridization chamber 204 includes the concentric apertures of the target wash well 254, valve plate 102 and manifold assembly 104, channels 216, 214, 212, 210, 224 and aperture 208. The second probe wash is routed from the hybridization chamber 204 to the waste well 270 through a conduit formed from aperture 206, channel 222, coincident apertures 200 and corresponding aperture in the valve plate 102 and lateral channel 201 to the waste well 270. The wash is urged from the second probe well 254 through the hybridization chamber 204 and into the waste well 270 via pneumatic pressure applied from the pump 500 through valve V2 and connection 54.

Following the probe wash, a first silver solution may be transferred from liquid well 262 into the sample well 268. In order to route the first silver solution into the sample well 268, the valve plate 102 may be moved to the −6.3 mm position (FIG. 4(*d*)).

In the −6.3 mm position, a conduit is formed between the silver well 262 and sample well 268. The conduit between the silver well 262 and sample well 268 includes the concentric apertures of the silver well 262, valve plate 102 and manifold assembly 104, channels 212, 210 and concentric apertures of the sample well 268, valve plate 102 and manifold assembly 104. The silver solution is moved from the silver well 262 into the sample well 268 via pneumatic pressure applied from the pump 500 through valve V7 and connection 62.

Next, a second silver solution may be transferred from a second silver well 260 into the sample well 268 for mixing with the first silver solution. In order to route the first silver solution into the sample well 268, the valve plate 102 may be moved to the −8.4 mm position (FIG. 4(*e*)).

In the −8.4 mm position, a conduit is formed between the silver well 260 and sample well 268. The conduit between the silver well 260 and sample well 268 includes concentric apertures at the bottom of the well 260 and aperture plate 102, channel 226, concentric apertures below the well 262 that connect the channel 226 and channel 212, channels 212, 210 and concentric apertures of the sample well 268, valve plate 102 and manifold assembly 104.

The silver solution is moved from the silver well 260 into the sample well 268 via pneumatic pressure applied from the pump 500 through valve V6 and connection 60. During the transfer, the sample well 268 may be vented to atmosphere by activating valve V11. Once transferred to the sample well 268, the solution may be mixed by deactivating valve V6 and activating valve V5 and then alternately activating valves V6 and V5.

The mixed silver solution in the sample well 268 may be transferred to the hybridization chamber 204 by moving the valve plate 102 to position −2.1 mm. The process of moving a liquid from the sample chamber 268 to the hybridization chamber 204 has been described above.

Once the silver solution has been transferred to the hybridization chamber 204, the hybridization chamber 204 may be rinsed and dried by moving the valve plate 102 to position −10.5 mm (FIG. 4(*f*)). In the −10.5 mm position, a conduit is formed between the rinse well 256 through the hybridization chamber 204 to the waste well 270. The conduit between the rinse well 256 and hybridization chamber 204 includes the concentric apertures of the rinse well 256, valve plate 102 and manifold assembly 104, channels 218, 216, 214, 212, 210, 224 and aperture 208. The rinse is routed from the hybridization chamber 204 to the waste well 270 through a conduit formed from aperture 206, channel 222, coincident apertures 200 and corresponding aperture in the valve plate 102 and lateral channel 201 to the waste well 270. The rinse is urged from the rinse well 256 through the hybridization chamber 204 and into the waste well 270 via pneumatic pressure applied from the pump 500 through valve V3 and connection 56.

Once the hybridization chamber 204 has been rinsed, it may be dried. Drying may be facilitated by the application of heat applied to the bottom of the module 14 by a heater 22. The heater 22 is activated during the portion of the processing by the CPU 16.

Drying may also be accelerated by introducing a stream of air through the hybridization chamber 204. In order to cause air to flow through the hybridization chamber 204, the valve plate 102 may remain in the −10.5 mm position and the pump 500 may continue to introduce compressed air through the rinse well 256 after the rinse well 256 has been emptied of rinse liquid. In the case where the pump 500 is a piston pump as shown in FIG. 5 and when the piston has depleted the air within the piston, the CPU 16 may deactivate valve V3 and activate valve 12. By activating valve V12, the piston may draw in additional air. Once the piston is fully retracted, the CPU 16 may deactivate valve V12 and reactivate valve V3. Once valve V3 is activated, the piston may again be advanced to introduce air into the hybridization chamber 204 through the rinse well 256 and which air exits through the waste well 270.

In use, a target DNA or RNA sample within the sample well 268 may be hybridized with an oligonucleotide within the hybridization chamber 204. Detection of the hybridized materials may be amplified by an autometallographic process where metal ions such as from silver nitrate are reduced to silver atoms that preferentially bind to nanoparticles within an oligonucleotide.

In preparation for testing for a particular nucleic acid, a first oligonucleotide or first group of oligonucleotides with a first predetermined genetic sequence may be disposed on the substrate 110 within the hybridization chamber 204. The first oligonucleotides may have a genetic sequence that is complementary to a first portion of the genetic sequence of the predetermined target nucleic acid.

A probe deposited within the probe well 264 may be constructed of nanoparticles with one or more strands of second oligonucleotides of a second predetermined genetic sequence attached to the nanoparticles. Nanoparticles useful in the practice of the invention may include metal (e.g., gold, silver, copper, and platinum), semiconductor (e.g., CdSe, CdS, and CdS or CdSe coated with ZnS) and magnetic (e.g., ferromagnetite) colloidal materials. Other nanoparticles useful in the practice of the invention include ZnS, ZnO, $TiO_2$, AgI, AgBr, $HgI_2$, PbS, PbSe, ZnTe, CdTe, $In_2S_3$, $Cd_3P_2$, $Cd_3As_2$, InAs, and GaAs. The size of the nanoparticles is preferably from about 5 nm to about 150 nm (mean diameter), more preferably from about 5 to about 50 nm, most preferably from about 10 to about 30 nm.

The nanoparticles, the second oligonucleotides or both are functionalized in order to attach the oligonucleotides to the nanoparticles. Such methods are known in the art. For instance, oligonucleotides functionalized with alkanethiols at their 3'-termini or 5'-termini readily attach to gold nanoparticles.

The second oligonucleotides may have a sequence that is complementary to a second portion of the genetic sequence of the predetermined target nucleic acid. Preparation of the First and Second Oligonucleotides and attachment to the respective particles and substrate may be accomplished generally as described in U.S. Pat. No. 6,417,340 assigned to the assignee of the present invention and incorporated herein by reference.

In general, the test sample of RNA or DNA (nucleic acid) may be denatured at a beginning of a test. Denaturing may be accomplished using any known process (e.g., heat, chemical, etc.).

The temperature of the contents of the sample well 268 and the hybridization chamber 204 may be carefully controlled to ensure a successful test. The contents of the sample well 268 may be heated to 95° C. for denaturation of the biomolecules (e.g., DNA). Heating of up to 130° C. may be provided for concentration of sample fluids via evaporation. The temperature control may be 95° C.+/−5° C. and 130° C.+/−10° C.

The probe may be mixed with a buffer by moving the probe from the probe liquid well 264 to the buffer well 266. The CPU 16 may do this by instructing the servo actuator 24 to move the valve plate 102 to the +4.2 mm position and activating the appropriate valves using the process described above with reference to FIG. 4(h). Alternatively, the probe may be transferred to the hybridization chamber 204, directly, as part of a separate process.

The denatured sample may be moved from the sample well 268 to the buffer well 266 and contents may be mixed. The CPU 16 may do this by instructing the servo actuator 24 to move the valve plate 102 to the −4.2 mm position and activating the appropriate valves using the process described above with reference to FIG. 4(c).

The mixed sample and buffer may be moved to the hybridization chamber 204. The CPU 16 may move the mixture to the hybridization chamber 204 by instructing the servo actuator 24 to move the valve plate 102 to the −2.1 mm position and activating the appropriate valves using the process described above with reference to FIG. 4(b).

The temperature of the hybridization chamber 204 is controlled by the heating/cooling device 22. the heating/cooling device 22 may be a series of Peltier thermoelectric elements to provide both heating and cooling with +/−1° C. The temperature can be varied by the heating/cooling device 22 as each step in the hybridization process is effected.

A shuttling motion may be used to facilitate hybridization. Shuttling may be accomplished by the CPU 16 instructing the servo actuator 24 to move the valve plate 102 to the home position 0.0 mm position and activating the appropriate valves using the process described above with reference to FIG. 4(a).

Following hybridization, one or more washing steps may occur with wash solutions. The CPU 16 may wash the hybridized sample by instructing the servo actuator 24 to move the valve plate 102 to the +8.4 mm position and activating the appropriate valves using the process described above with reference to FIG. 4(j).

If a probe was not included in the sample, then a probe solution can be added following the first wash and a probe hybridization may follow over a predetermined time period determined by the controller 16. The probe may be transferred to the hybridization chamber 204 by the CPU 16 first moving the valve plate to the +4.2 mm position and activating the appropriate valves (as described in conjunction with FIG. 4(h)) and then by moving the valve plate 102 to the −2.1 mm position and activating the appropriate valves (as described in conjunction with FIG. 4(b)).

Probe hybridization may be accomplished using a shuttle operation described in conjunction with the home position of the valve plate 102. The probe hybridization may be of a duration of between 5 to 30 minutes depending upon the application.

Another series of washes can be performed following the probe hybridization. The CPU 16 may perform the washes by instructing the servo actuator 24 to first move the valve plate 102 to the +8.4 mm and then the +10.5 mm positions and activating the appropriate valves using the processes described above with reference to FIGS. 4(j) and 4(k).

One or more solutions can be added during each processing phase. Typically one solution is added except for during probe hybridization and signal amplification when two solutions may be added in parallel. When a single solution is to be added, the CPU 16 may instruct the servo 24 to move the valve plate 102 to the −6.3 mm position and then the −2.1 mm position and activate the appropriate valves in sequence as described in conjunction with FIG. 4(d) and FIG. 4(b). When two solutions are to be added, the CPU 16 may instruct the servo 24 to move the first solution to the sample well 268 using valve position −6.3 mm and the appropriate valves and then move the second solution to the sample well 268 using valve position −8.3 mm and the appropriate valves. The two solutions may be mixed using the process described in conjunction with FIG. 4(e).

Once the detected sample has been amplified, the amplified sample may be rinsed and dried. Rinsing may be accomplished by the CPU 16 using valve position −10.5 mm and the appropriate valves. Drying can be accomplished using the process described in conjunction with FIG. 4(f).

A specific embodiment of a disposable sample processing module has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A system for processing a nucleic acid comprising:
a disposable self-contained processing module, the disposable self-contained processing module further comprising a sample well, a valve plate, a manifold assembly and a substrate assembly stacked one on top of another with the substrate assembly occupying a bottom of the stack, the manifold assembly mounted on top of the substrate assembly, the sample well mounted on top of the manifold assembly with the valve plate slidably disposed between the manifold assembly and sample well and adapted to laterally slide as a single unit relative to the manifold assembly and sample well, the substrate assembly further comprising a substrate where the substrate and manifold assembly together define a hybridization chamber between the substrate and manifold assembly, the manifold assembly further comprises a plurality of channels between the hybridization chamber and an opposing side of the manifold assembly, the sample well further comprises a plurality of liquid wells each with a first aperture on an outside surface of the disposable self-contained processing module and a second aperture on a side of the sample well facing the slidable valve plate and where the slidable valve plate further comprises a plurality of sets of channels extending through the valve plate from the sample well side to the manifold assembly side, the slidable valve plate having a plurality of predetermined positions with respect to the sample well and manifold assembly, where each position of the plurality of positions forms a different set of fluid connections between respective one or more of the liquid wells of the sample well and the hybridization chamber through the valve plate and manifold assembly.

2. A system for processing a nucleic acid comprising:
a disposable self-contained processing module that contains the nucleic acid and substantially all of the fluids to effect a nanoparticle hybridization test;
a pump coupled to the processing module;
a valving system disposed between the pump and processing module; and
a control system coupled to the pump and valving system causing the processing fluids to interact with the nucleic acid to effect a sandwich hybridization test using nanoparticles
a plurality of respective liquid wells disposed in a body of the processing module for holding liquids used for processing the nucleic acid;
a hybridization chamber for hybridizing the nucleic acid; and
a valve plate disposed between the plurality of liquid wells and the hybridization chamber, said valve plate having a plurality of positions that each faun respective channels that communicate liquids between at least some of the liquid wells and the hybridization chamber.

3. The disposable, self-contained processing module as in claim 2 further comprising a manifold assembly disposed between the valve plate and hybridization chamber that routes the liquids between the valve plate and the hybridization chamber.

4. The disposable, self-contained processing module as in claim 3 wherein the manifold assembly further comprises a manifold base with a first surface that engages the valve plate and a second opposing surface with a plurality of channels disposed on the second surface and a plurality of apertures extending from respective channels of the plurality of channels through the manifold plate and wherein at least some of the plurality of apertures in the manifold plate are aligned concentrically with respective liquid wells on the plurality of liquid wells on an opposite sides of the valve plate.

5. The disposable, self-contained processing module as in claim 4 further comprising a manifold cover disposed on the second side of the manifold plate with a first side of the manifold cover disposed against the second side of the manifold plate in an abutting relationship with the plurality of channels and a second side of the manifold cover forming a first wall of the hybridization chamber, said manifold cover having a plurality of apertures with each aperture of the plurality of apertures joining a respective channel of the plurality of channels on the first side of the manifold cover and the hybridization chamber on the second side of the manifold cover.

6. The disposable, self-contained processing module as in claim 5 further comprising a substrate disposed against the second side of the manifold cover to form a second, opposing second wall of the hybridization chamber.

7. The disposable, self-contained processing module as in claim 6 further comprising an oligonucleotide disposed on the substrate within the hybridization chamber.

8. The disposable, self-contained processing module as in claim 4 wherein the valve plate further comprises a plurality of apertures extending through the valve plate wherein when the valve plate is in a first position of the plurality of positions, the plurality of apertures forms a portion of a liquid passageway between at least two of the plurality of liquid wells.

9. The disposable, self-contained processing module as in claim 8 further comprises when the valve plate is in a second position of the plurality of positions, the plurality of apertures forms a portion of a liquid passageway between a liquid well of the plurality of liquid wells and the hybridization chamber.

10. The disposable, self-contained processing module as in claim 2 wherein each of the plurality of sample wells further comprise a pressure connection for pressurizing the sample well from an external source.

11. The disposable, self-contained processing module as in claim 2 further comprising an external shuttle connection.

12. The disposable, self-contained processing module as in claim 11 wherein the plurality of valve plate positions further comprises a shuttle position for shuttling a liquid back and forth through the hybridization chamber.

13. The disposable, self-contained processing module as in claim 2 wherein the plurality of valve plate positions further comprising a sample transfer position that transfers a nucleic sample from a liquid well of the plurality of liquid wells into the hybridization chamber.

14. The disposable, self-contained processing module as in claim 2 wherein the plurality of valve plate positions further comprises a liquid well transfer position that transfers liquids from a first liquid well of the plurality of liquid wells to a second liquid well of the plurality of liquid wells.

15. The disposable, self-contained processing module as in claim 2 wherein the plurality of valve plate positions further comprises a wash position that transfers a wash or silver solution from a first liquid well of the plurality of liquid wells through the hybridization chamber to a waste well of the plurality of liquid wells.

16. A system for processing test samples comprising:
a low-cost, disposable, self-contained microfluidics processing module for processing the test sample:

a plurality of liquid wells disposed in a body of the low-cost, disposable, self-contained microfluidics processing module adapted to contain reagents for processing the test sample;

a chamber for hybridizing the test sample disposed within the processing module; and a valve plate disposed between the plurality of liquid wells and the chamber, said valve plate being moveable as a single unit laterally with respect to the liquid wells and the chamber among a plurality of positions that each form respective, microfluidics channels that communicate liquids between at least some of the liquid wells and the chamber.

17. The system for processing test samples as in claim 16 further comprising a servo actuator coupled to the valve plate that moves the valve plate among the plurality of positions.

18. The system for processing test samples as in claim 16 wherein a first position of the plurality of positions of the valve plate further comprises a microfluidics channel between two liquid wells of the plurality of liquid wells.

19. The system for processing test samples as in claim 16 wherein a second position of the plurality of positions of the valve plate further comprises a microfluidics channel between a liquid well of the plurality of liquid wells and the chamber.

20. A system for processing test samples comprising:
a low-cost, disposable, self-contained microfluidics processing module for processing the test sample:
a plurality of liquid wells disposed in a body of the low-cost, disposable, self-contained microfluidics processing module adapted to contain reagents for processing the test sample;
a chamber for hybridizing the test sample disposed within the processing module; and
a valve plate disposed between the plurality of liquid wells and the chamber, said valve plate being moveable among a plurality of positions that each form respective, microfluidics channels that communicate liquids between at least some of the liquid wells and the chamber;
a servo actuator coupled to the valve plate that moves the valve plate among the plurality of positions wherein a first position of the plurality of positions of the valve plate further comprises a microfluidics channel between two liquid wells of the plurality of liquid wells wherein a second position of the plurality of positions of the valve plate further comprises a microfluidics channel between a liquid well of the plurality of liquid wells and the chamber; and
a pump with a plurality of outputs coupled to the processing module that pumps the respective reagents through the plurality of microfluidics channels.

21. The system for processing test samples as in claim 20 further comprising a central processing unit coupled to the servo actuator and pump that controls an order of the sequentially provided microfluidics channels and pumping of the reagents through the microfluidics channels.

22. The system for processing test samples as in claim 21 wherein the pump further comprises a solenoid valve manifold having a plurality of outputs.

23. The system for processing test samples as in claim 22 wherein the plurality of liquid wells further comprise a respective liquid well for the test sample and each of the respective reagents.

24. The system for processing test samples as in claim 23 further comprising a processing module coupler that couples at least some of the plurality of outputs of the solenoid valve manifold to respective liquid wells of the plurality of liquid wells.

25. The system for processing test samples as in claim 24 wherein the processing module coupler further comprises a connection for shuttling a liquid back-and-forth within the hybridization chamber.

26. The system for processing test samples as in claim 25 wherein the processing module further comprises a waste well.

27. The system for processing test samples as in claim 26 wherein the plurality of positions further comprises a first position that couples a first liquid well to the an inlet of the hybridization chamber and an outlet of the hybridization chamber to the waste well.

28. A method for processing a nucleic acid comprising:
providing a disposable self-contained processing module that contains a hybridization chamber, then nucleic acid and a plurality of processing liquids for processing the nucleic acid within the hybridization chamber;
sequentially creating a plurality of liquid flow conduits within the processing module among the nucleic acid, the plurality of processing liquids and the hybridization chamber by moving a valve plate to a predetermined position that corresponds to a respective conduit of the plurality of conduits; and
pumping the respective processing liquids through the sequentially created plurality of liquid flow conduits.

29. The method of processing the nucleic acids as in claim 28 further comprising disposing the nucleic acid and a plurality of processing liquids in respective liquid wells.

30. The method of processing the nucleic acids as in claim 29 wherein the step of pumping further comprises pressurizing the respective liquid wells.

31. The method of processing the nucleic acids as in claim 28 wherein the step of pressurizing the respective liquid wells further comprises using pneumatic pressure.

32. The method of processing the nucleic acids as in claim 29 wherein the step of pumping further comprises sequentially pressurizing the respective liquid wells.

33. The method of processing the nucleic acids as in claim 28 further comprising internally storing waste products of the process within the processing module.

* * * * *